United States Patent [19]

Thomas

[11] Patent Number: 5,658,937
[45] Date of Patent: Aug. 19, 1997

[54] EFFECTIVE TREATMENT MODALITY FOR INFECTIOUS DISEASES, PULMONARY CONDITONS AND SEQUELAE THEREOF

[75] Inventor: Peter G. Thomas, Charlottesville, Va.

[73] Assignee: Cytos Pharmaceuticals LLC, Durham, N.C.

[21] Appl. No.: 316,326

[22] Filed: Sep. 30, 1994

Related U.S. Application Data

[62] Division of Ser. No. 17,766, Feb. 16, 1993, Pat. No. 5,352, 691.

[51] Int. Cl.$^6$ .................................................. A61K 31/415
[52] U.S. Cl. ........................................ 514/400; 514/385
[58] Field of Search ........................................ 514/385, 400

[56] References Cited

U.S. PATENT DOCUMENTS

| | | | |
|---|---|---|---|
| 3,746,700 | 7/1973 | Parisi et al. | 548/101 |
| 3,988,466 | 10/1976 | Takagi et al. | 514/561 |
| 3,995,051 | 11/1976 | Cook et al. | 514/400 |
| 4,332,814 | 6/1982 | Newsome et al. | 424/273 |
| 4,339,378 | 7/1982 | Masaki et al. | 260/112.5 R |
| 4,342,774 | 8/1982 | Okabe et al. | 424/273 R |
| 4,508,728 | 4/1985 | Nagai et al. | 424/273 |
| 4,734,276 | 3/1988 | Ziegler | 424/10 |
| 4,863,900 | 9/1989 | Pollock et al. | 514/12 |
| 5,030,645 | 7/1991 | Kollonitsch | 514/396 |
| 5,238,931 | 8/1993 | Yoshikawa et al. | 514/184 |
| 5,280,038 | 1/1994 | Kukreja et al. | 514/400 |

FOREIGN PATENT DOCUMENTS 0 466 029 B1   1/1992   European Pat. Off. .

OTHER PUBLICATIONS

Shenkar et al., "Effects of treatment with the 21-aminosteroid, U74389F, on pulmonary cytokine expression following hemorrhage and resuscitation," Critical Care Medicine 23(1):132–139 (1995).

Grimble, "Malnutrition and the immune response 2. Impact of nutrients on cytokine biology in infection," Transactions of the Royal Society of Tropical Medicine and Hygiene 88:615–619 (1994).

Grimble, "Nutritional Antioxidants and the Modulation of Inflammation: Theory and Practice," New Horizons 2(2):175–185 (1994).

Kelly et al., "Dimethyl Sulfoxide Modulates NF-κB and Cytokine Activation in Lipopolysaccharide-Treated Murine Macrophages," Infect. Immun. 62(8):3122–3128 (1994).

Simpson et al., "Acute Fulminant Stage Adult T-Cell Leukemia/Lymphoma in Rabbits Inoculated with an HTLV-1 Transformed Rabbit Cell Line," Journal of Acquired Immune Deficiency Syndrome 6(6):741 (1993).

Eugui et al., "Some antioxidants inhibit, in a co-ordinate fashion, the production of tumor necrosis factor–α, IL–β, and IL–6 by human peripheral blood mononuclear cells," Int'l Immunol. 6(3):409–422 (1993).

Bone, "Inhibitors of complement and neutrophils: A critical evaluation of their role in the treatment of sepsis," Critical Care Medicine 20(6):891–898 (1992).

Erickson et al., "Influence of Histidine on Lipid Peroxidation in Sacroplasmic Reticulum," Archives of Biochemistry and Biophysics 292(2):427–432 (1992).

Fujimoto et al., "Histamine and histidine decarboxylase are correlated with mucosal repair in rat small intestine after ischemia-reperfusion," abstract, J. Clin. Invest. 89(1):126–133 (1992).

Maldonade et al., "Specific Serum Amino-acid Profiles of Trauma and Septic Children," Clin. Nutr. 7(3):165–170 (1988).

Gebhard et al., "Bretschneider's Histidine-Buffered Cardioplegic Solution: Concept, Application, and Efficiency," Myocardial Protection in Cardiac Surgery, pp. 95–119 (1987).

Harvey et al., "Dietary $_L$-Histidine-Induced Hypercholesterolemia and Hypocupremia in the Rat$^{1,2}$," J. Nutri. 111(4):639–647 (1981).

Spector et al., "Stimulation of mucosal growth by gastric and ileal infusion of single amino acids in parenterally nourished rats," abstract, Digestion 21(1):33–40 (1981).

Askanazi et al., "Muscle and Plasma Amino Acids Following Injury," Annl. Surg. 192(1):78–85 (1980).

Ferrante et al., "Optimal Conditions for Simultaneous Purification of Mononuclear and Polymorphonuclear Leucocytes from Human Blood by the Hypague-Ficoll Method," J. Immunol. Meth. 36:109–117 (1980).

Schlech et al., 1985, JAMA, 253:1749–54.

Tunkel et al., 1990, Annals of Int. Med. 112:610–623.

Cheson et al., 1976, J. Clin. Invest. 58:789–796.

Allen et al., 1976, Biochem. Bosphys. Res. Comm. 69:245–252.

Chang et al., 1987, Journal of Clinical Investigation 79:1498–1509.

Horgan, et al., 1990, American Journal of Physiology 259:L315–L319.

McMurtry et al., 1976, Circulation Research 38:99–104.

Brashers, et al., 1988, Journal of Clinical Investigation 82:1495–1502.

Dawson, et al.; "Pulmonary microcirculatory hemodynamics"; Annals of the New York Academy of Sciences 384:90–106, 1982.

(List continued on next page.)

Primary Examiner—Theodore J. Criares
Attorney, Agent, or Firm—Isaac Angres; Susan Petraglia

[57] ABSTRACT

A treatment modality for infectious diseases and pulmonary conditions that result from the inflammatory responses by tissues to infections by microorganisms, including but not limited to viruses, retroviruses, bacteria, or other microorganisms, or toxins that arise from microorganisms comprises administering an effective amount of histidine to the affected subject to combat the disease or the distress condition resulting therefrom.

8 Claims, 4 Drawing Sheets

OTHER PUBLICATIONS

Sawasdikol et al.; "Infection of the Laboratory Rabbit with HIV-1 and HTLV-1"; AIDS Research Reviews, 2:211-233, 1992.

Kindt et al.; "Acute Mononuclear Cell Leukemia in Outbred Rabbits Inoculated with HTLV-I Transformed Rabbit Lines"; Int'l Cong. Immun., Aug., 1992.

Sawasdikol et al.; "Acute Mononuclear Cell Leukemia in Outbred Rabbits Inoculated with HTLV-I Transformed Rabbit Cell Lines"; FASEB J., Part II, vol. 6, No. 5, Apr. 5-9, 1992.

R. Berkow; The Merck Manual of Diagnosis and Therapy, 1982; pp. 54-57.

Quagliarello et al.; "Morphologic Alterations of the Blood-Brain Barrier with Experimental Meningitis in the Rat"; J. Clin. Invest. 77:1084-1095, 1986.

Wispelwey et al.; "Haemophilus influenzel Lipopolysaccharide-induced Blood Brain Barrier . . . in the Rat"; J. Clin. Invest. 82:1339-1346; 1988.

Quagliarello et al.; "Bacterial Meningitis: Pathogenesis, Pathophysiology, and Progess"; New England Journal of Medicine, Sep. 17, 1992, pp. 864-872.

Kindt, et al.; "Acute Mononuclear Cell Leukemia in Outbred Rabbits Inoculated with HTLV-I Transformed Rabbit Lines"; Int'l. Congress of Immunology, Aug. 1992 (Abst).

Powell et al.; "Effect of Oxygen-Free Radical Scavengers on Survival in Sepsis" The Amer. Surgeon 57(2) Feb. 1991, pp. 86-88.

Baruchel et al.; "The role of oxidative stress in disease progression in individuals ifected by the human immunodeficiency virus"; Journal of Leukocyte Biology, vol. 52, Jul. 1992, pp. 111-114.

Chang et al.; "Beneficial effect of a platelet-activating factor antagonist, WEB 2086, on endotoxin-induced lung injury"; 1990, American Physiological Society, pp. H153-H158.

Bone; "Inhibitors of complement and neutrophils: A critical evaluation of their role in the tratment of sepsis"; Critical Care Medicine, vol.20, No.6,pp.891-898.

Erickson et al.; "Influence of Histidine on Lipid Peroxidation in Sarcoplasmic Reticulum"; Archives of Biochem. and Biophysics; Vo. 292, No. 2 pp. 427-482.

Harvey et al.; "Dietary L-Histidine-Induced Hypercholesterolemia and Hypocup-remia in the Rat"; Dept. of Food Science and Nutrition, Colorado State Univ.; (Abstract).

Askanazi et al.; Ann. Sovg. 192(1):78-85 (1980), Dialoge Date Base Abstract Only #80178866 Embase file. (Cite from Examiner Hook, Paper No. 2 of Parent).

Maldonado et al "Clin. Nutr." 7(3): 165-170 (1988); Dialogue Data Base Abstract Only #88196647 Embase file.

EFFECTIVE TREATMENT MODALITY FOR INFECTIOUS DISEASES, PULMONARY CONDITONS AND SEQUELAE THEREOF

This application is a divisional of application Ser. No. 08/017,766, filed on Feb. 16, 1993, now U.S. Pat. No. 5,352,691.

BACKGROUND OF THE INVENTION

1. Field of the Invention

The present invention is related generally to methods of treating infectious diseases and pulmonary conditions. More particularly, the present invention is related to providing an effective treatment modality to combat infectious diseases and/or pulmonary distress conditions by administering histidine or its salts, analogs or derivatives to the affected subject.

2. Description of the Prior Art

Various treatment modalities, including drug and antibiotic therapy, are known for combating pulmonary conditions and infectious diseases, both viral and bacterial. However, morbidity and mortality from infectious diseases and respiratory distress remain high despite recent advances in therapeutics. For instance, mortality rates associated with three common causative agents of bacterial meningitis, viz., *Haemophilus influenzae*, *Neisseria meningitides*, and *Streptococcus pneumonias*, were 6.0%, 10.3%, and 26.3%, respectively, in the USA from 1978–1981 (Schlech et al., 1985, *JAMA*, 253: 1749–54). Mortality rates have not changed significantly during the last 30 years, and in children and adults who survive bacterial meningitis, there is a high incidence of neurologic sequelae (Tunkel et al., 1990, *Annals of Int. Med.* 112: 610–623).

Treatment of disease conditions arising from acquired immune disease syndrome (AIDS) and human T-cell leukemia (HTLV) series of viruses remains a problem and much progress needs to be made in these areas.

SUMMARY OF THE INVENTION

According to the invention, it has been discovered that the therapeutic administration of histidine, its salts, analogs or derivatives, to humans and animals can provide protection from or ameliorate the damage that results from inflammatory responses by tissues to infections by microorganisms, including but not limited to viruses, retroviruses, bacteria, or other microorganisms or parasites, or toxins that arise from microorganisms or parasites. Hence, histidine administration can be used as an effective treatment for pulmonary conditions, infectious diseases or effects thereof.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
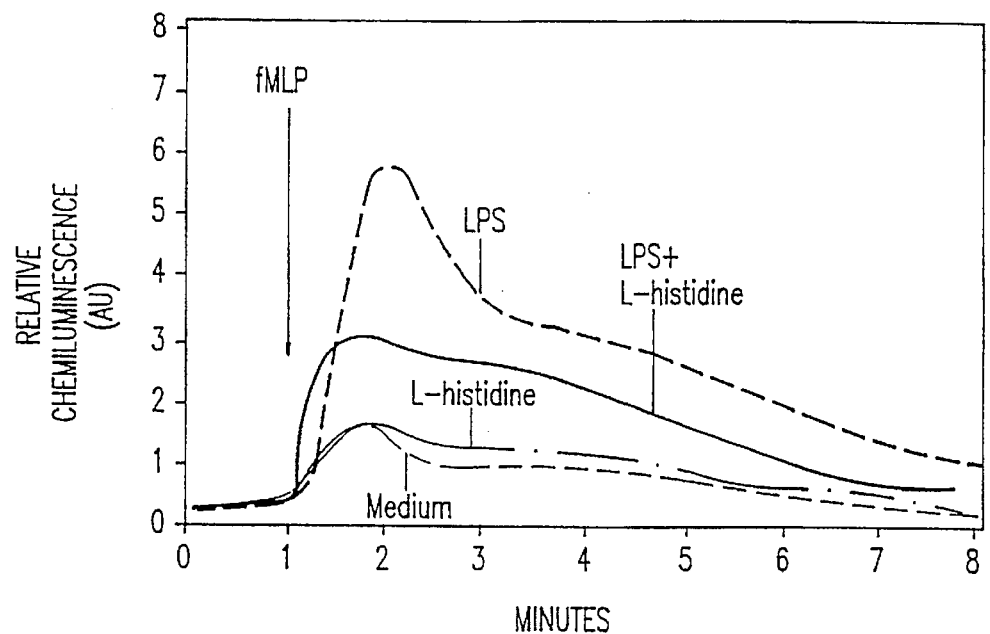
FIG. 1 is a graph showing the relative chemiluminescence of histidine treated and untreated human polymorphonuclear (PMN) leukocytes primed with lipopolysaccharide (LPS) endotoxin and stimulated with the chemoattractant peptide f-met-leu-phe (fMLP)

This invention is particularly directed to the use of histidine, its salts, derivatives or analogs, as therapeutic agents to combat pulmonary or infectious diseases or conditions resulting therefrom. The term "pulmonary condition" as used herein means both infection and non-infection induced inflammatory conditions of the lungs and, particularly, any condition characterized by oxidative stress and/or damage in the lungs. For example, tuberculosis, cystic fibrosis, adult respiratory distress syndrome (ARDS), septic shock, pneumonia, asthma, etc., may all be conditions in which the lungs are subject oxidative stress and/or damage. The term "combatting" as used herein included protecting against and/or treating to ameliorate the damage resulting from inflammation or inflammatory responses of tissues. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the methods and materials described herein are preferred. Unless mentioned otherwise, the techniques employed or contemplated herein are standard methodologies well known to one of ordinary skill in the art. The materials, methods and examples are only illustrative and not limiting.

Histidine can be administered by a wide variety of means including topical, oral, and intravenous and intraperitoneal injection delivery routes. Intraperitoneal injection was used in the in vivo experiments discussed below, and may be the preferred mode of administration for a number of infectious diseases or pulmonary conditions. However, topical administration to the lungs via an oral or nasal metered dose inhaler (MDI), dry powder inhaler, or nebulizer may be advantageous in treating certain conditions such as cystic fibrosis. Histidine can be administered as either D- or L-histidine in pure form, or it may be provided as a salt (ammonium salts, sodium salts, lithium salts, alkaline earth and metal salts, etc.), derivative or analog. Preferably, salts, derivatives and analogs of histidine used in the practice of this invention would be easily reduced to L-histidine by conditions in the body. Histidine could be provided in many different and conventional pharmaceutically acceptable formulations, including: elixirs, syrups, water and other liquid diluents, buffers and agents which render an injectable composition isotonic, solid diluents and excipients such as lactose starch, conventional disintegrating agents, coatings and the like, freon gases and other propellants used in MDIS, etc.

The dosage of histidine can vary widely and depends both on the patient and the disease or condition being treated. A common dosage regime may include administering 10–100 mg/kg body weight every four hours. Since histidine has a short half-life, chronic administration of histidine will not result in progressive plasma level accumulation. Experimental evidence has shown that human subjects ingesting a 4.5 gram oral dose of histidine per day over a thirty week time period only resulted in an average increase of histidine of 8.5% above baseline. While some reports on the chronic administration of L-histidine have shown that histidine chelates zinc, and may cause hypercholesterolemia and/or hypocupremia, adding zinc, copper and/or arginine to the histidine formulation could aid in preventing these disease states.

The following Examples demonstrate the beneficial effects of histidine in the treatment of infectious diseases and pulmonary conditions in humans and animals.

EXAMPLE 1

This Example details experimental results which demonstrate the therapeutic effect of histidine on endotoxin primed oxidative activity of human neutrophils.

Materials:

Luminol, f-Met-Leu-Phe (fMLP), and human leukocyte myeloperoxidase (MPO) were obtained from Sigma Chemical, St. Louis, Mo. Ficoll-hypaque was purchased from Flow Laboratories (McLean, Va.), Accurate Scientific (Hicksville, N.Y.) and Los Alamos Diagnostics (Los Alamos, N. Mex.). Hanks balanced salt solution (HBSS) was obtained from Whittaker Bioproducts (Walkersville, Md.). Human serum albumin (HSA) was obtained from Cutter Biological (Elkhart, Ind.). Pyrogen-free L-histidine was supplied by Westmoreland Pharmaceuticals (Charlottesville, Va.). Lipopolysaccharide (LPS) endotoxin from *E. coli* (K235 strain) was purchased from List Biological Laboratories Campbell, Calif.

Neutrophil Preparation:

Purified human polymorphonuclear leukocytes (PMN) (~87% PMN and >95% viable by trypan blue exclusion) containing less than one platelet per five PMN and less than fifty pg/ml endotoxin (determined by limulus amebocyte lysate assay) were obtained from normal heparinized (10 Units/m.) venous blood by a one step ficoll-hypaque separation procedure (Ferrante, A. and Y. H. Thong, 1980, *J. Immunol. Meth.* 36: 109–117). Residual red blood cells (RBC) were lysed by hypotonic lysis with 3 ml iced 0.2% sodium chloride solution for 45 seconds followed by 0.8 ml 3% sodium chloride solution for the PMN chemiluminescence assays.

Neutrophil Chemiluminescence

Luminol enhanced chemiluminescence is a measure of PMN oxidative activity including singlet oxygen release (Cheson et al., 1976, *J. Clin. Invest.* 58: 789–796). Chemiluminescence was measured by a procedure modified from Allen, R. C. and L. D. Loose (1976, *Biochem. Biophys. Res. Comm.* 69: 245–252). Purified PMN ($1 \times 10^6$/ml were incubated (37° C. for 90 min) in 1 ml of diluent (HBSS-0.1% HSDA-1% autologous human heat-inactivated serum) with or without endotoxin (100 ng/ml) and with or without L-histidine (130 µM-40 mM). Luminol (500 µM) was then added and the cells transferred to a vial (37° C.) with a stirring bar. Chemiluminescence was read with a photometer for example a Chronolog® Photometer, (Havertown, Pa.) for one minute in the absence of fMLP, then fMLP (1 µM) was added and the chemiluminescence assay continued for seven more minutes. The relative chemiluminescence (area under the curves) was determined by weighing cut chart paper. The results are reported as relative fMLP-stimulated PMN chemiluminescence in arbitrary units (AU). The relative chemiluminescence was also determined as peak chemiluminescence in arbitrary light units (AUP) as indicated. Cell-free luminol enhanced chemiluminescence was generated by incubating MPO ($1.5 \times 10^{-4}$ mg/ml) with hydrogen peroxide ($4.5 \times 10^{-2}$ mg/ml) and luminol (500 µM) in HBSS. A cell-free dose response (L-histidine 1 µM–40 mM) was conducted to determine the therapeutically effective concentration of histidine.

Results

Priming of PMN chemiluminescence by LPS:

Tests showed that serum was necessary for effective priming of human PMN by LPS. Maximal priming was observed with an endotoxin concentration of 100 ng/ml and effective priming was observed after 90 min incubation with endotoxin.

FIG. 1 shows the relative chemiluminescence for four PMN leukocyte samples stimulated with fMLP at 1 µm after one minute. The sample primed with LPS at 100 ng/ml had a significantly larger relative chemiluminescence compared to the sample primed with the same amount of LPS, but which had L-histidine added thereto at 40 mM. The samples containing only the PMN leukocytes (medium) and 40 mM L-histidine and the PMN leukocytes (L-histidine) had insignificant chemiluminescence.

Figure 2A:
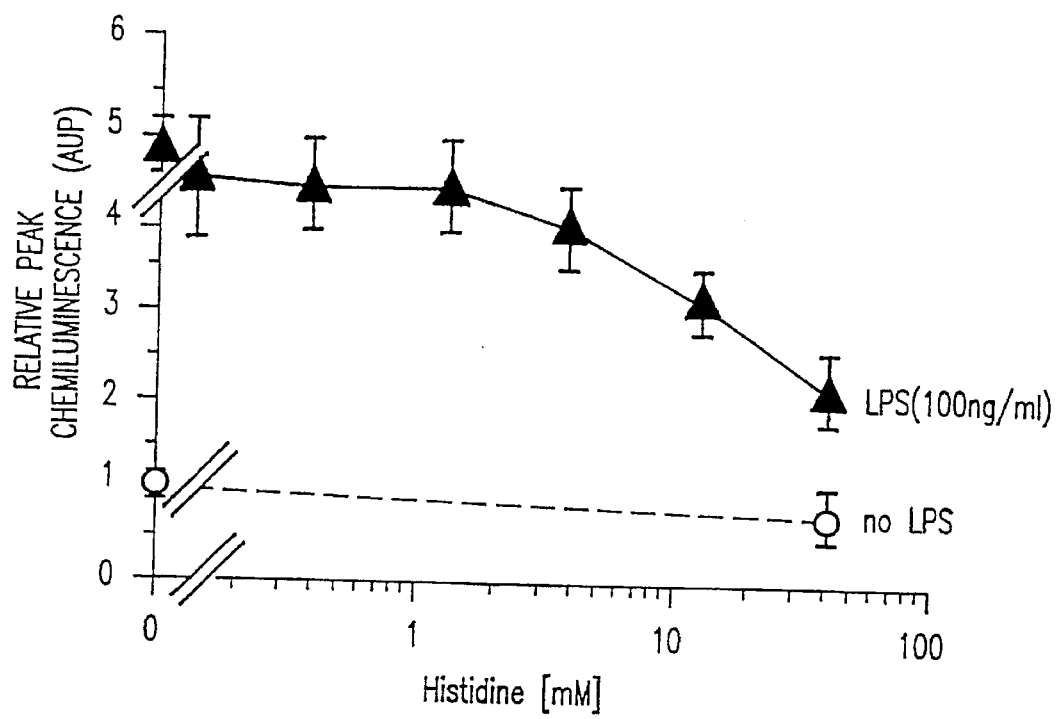
FIGS. 2a and 2b are graphs showing the chemiluminescence and relative peak chemiluminescence of LPS primed and unprimed PMN leukocytes.
Figure 2B:
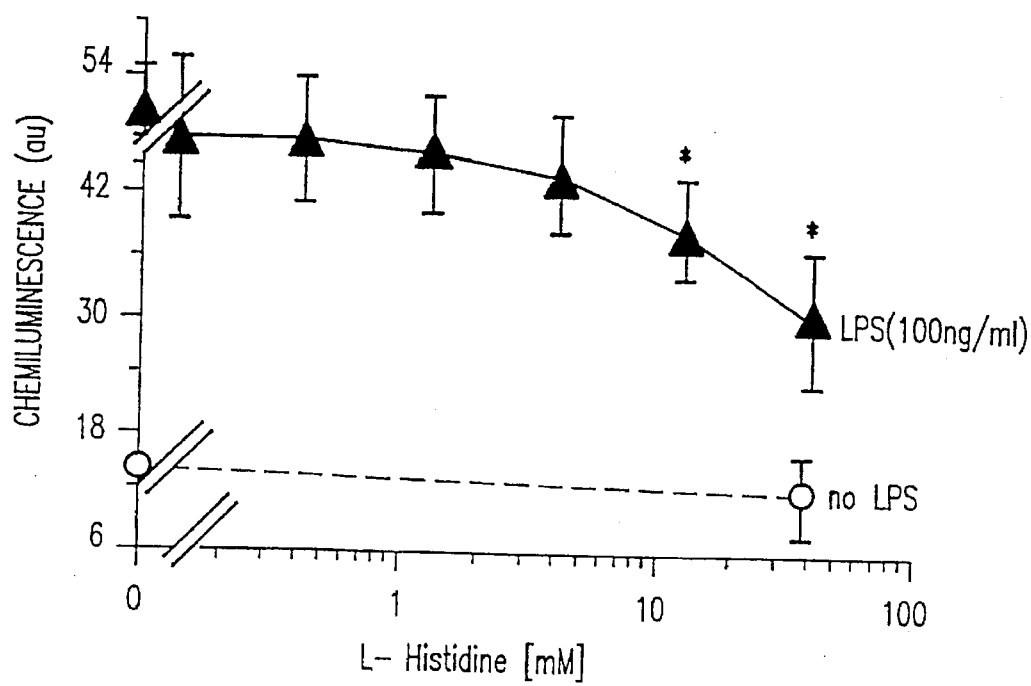

FIGS. 2a and 2b show that higher doses of L-histidine drive down chemiluminescence in LPS (100 ng/ml) endotoxin primed PMN oxidative activity and confirm that L-histidine (40 mM) had no effect on non-primed (no LPS) oxidative activity stimulated by fMLP. FIG. 2a shows that LPS (100 ng/ml for ninety minutes) primed PMN for increased chemiluminescence in response to fMLP (from 14±2 to 50±5 AU; p<0.001). FIG. 2b shows that L-histidine (13 mM and 40 mM) significantly decreased LPS endotoxin primed fMLP stimulated PMN oxidative activity (p=0.035 and p=0.001, respectively).

Figure 3:
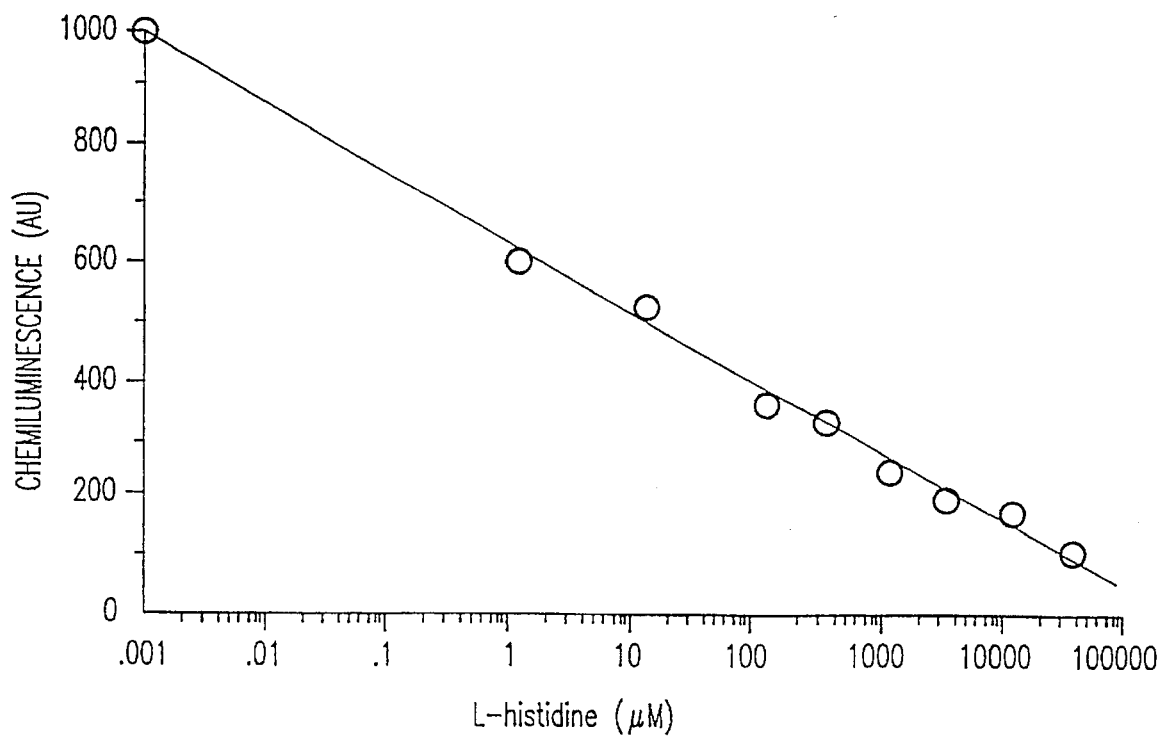
FIG. 3 is a graph showing the relative chemiluminescence of LPS primed and fMLP stimulated PMN leukocytes with different concentrations of L-histidine.

FIG. 3 shows that L-histidine (1.3µm–40 mM) decreased $MPO\text{-}H_2O_2$-halide chemiluminescence in a cell-free system. Hence, L-histidine has a therapeutic effect against tissue damaging oxygen species both inside and outside cells.

EXAMPLE 2

This Example details experimental results which demonstrate the therapeutic effect of histidine against *H. influenzae* or lipooligosaccharide (LOS) endotoxin induced meningeal inflammation.

In the experiments, adult rats (approximately 125–150 gms) of either sex were anesthetized with ketamine and xylazine. Their cisterna magna was punctured percutaneously with a 25 gauge needle fitted in a micromanipulator. After withdrawal of approximately 25 microliters of normal cerebrospinal fluid (CSF), the inoculum (*H. influenzae* or LOS) was injected. *H. influenzae* strain DL42 and LOS are prepared from strain DL42, which is a representative clinical isolate and a member of the most common group responsible for meningitis in humans.

One part of the experiment was directed to determining the percentage blood brain barrier permeability (BBBP) in rats infected with bacterial meningitis (*H. influenzae* strain DL42) which had been treated or not treated with L-histidine. Blood-brain barrier permeability (BBBP) to an exogenous protein is monitored by the traversal of iodine-labelled ($I^{125}$) bovine serum albumin (BSA) into the CSF. The histidine treated rats and control rats received a 250 mg/kg intraperitoneal injection of L-histidine. The histidine treated rats were also divided into two separate groups where one group received histidine simultaneously with the *H. influenzae* inoculum and the other group received histidine seventeen hours subsequent to the *H. influenzae* inoculum. The treated and untreated rats both received a $10^6$ cell dose of *H. influenzae* strain DL42. All BBBP percentages were measured eighteen hours after the *H. influenzae* inoculumusing $I^{125}$ labelled BSA. Table 1 presents the measured BBBP percentages.

TABLE 1

|  | Control | Untreated | Treated[a] T = 0[b] | Treated[a] T = 17[c] |
|---|---|---|---|---|
| Mean ± S.D. | 0.1 ± 0.1 | 4.39 ± 2.86 | 1.16 ± 0.7 | 1.129 ± .786 |
| Range | 0.06–0.21 | 0.42–9.9 | 0.12–1.9 | 0.41–2.5 |
| No. Rats | 2 | 12 | 5 | 7 |

[a]"T" is the time of IP histidine injection (either simultaneous with (T = 0) or seventeen hours subsequent (T = 17) to infection with *H. influenzae*.
[b]P = 0.005
[c]P = 0.001

Table 1 shows a significant difference in BBBP between the histidine treated and untreated rats. Furthermore, Table 1 shows that rats receiving an intraperitoneal injection even at seventeen hours subsequent to infection with *H. influenzae* had reduced BBBP percentages near the level of rats that received histidine at the time of infection. Hence, these results demonstrate that histidine can both protect against and treat bacterial meningitis (e.g., Table 1 shows that histidine prevents and reduces BBBP).

Another part of the experiment involved CSF pleocytosis. CSF is monitored by counting the CSF leukocyte concentration in a hemocytometer. Approximately 20 nanograms of intracisternally administered LOS will produce a maximal response in terms of CSF pleocytosis four hours subsequent to LOS administration.

Figure 4:
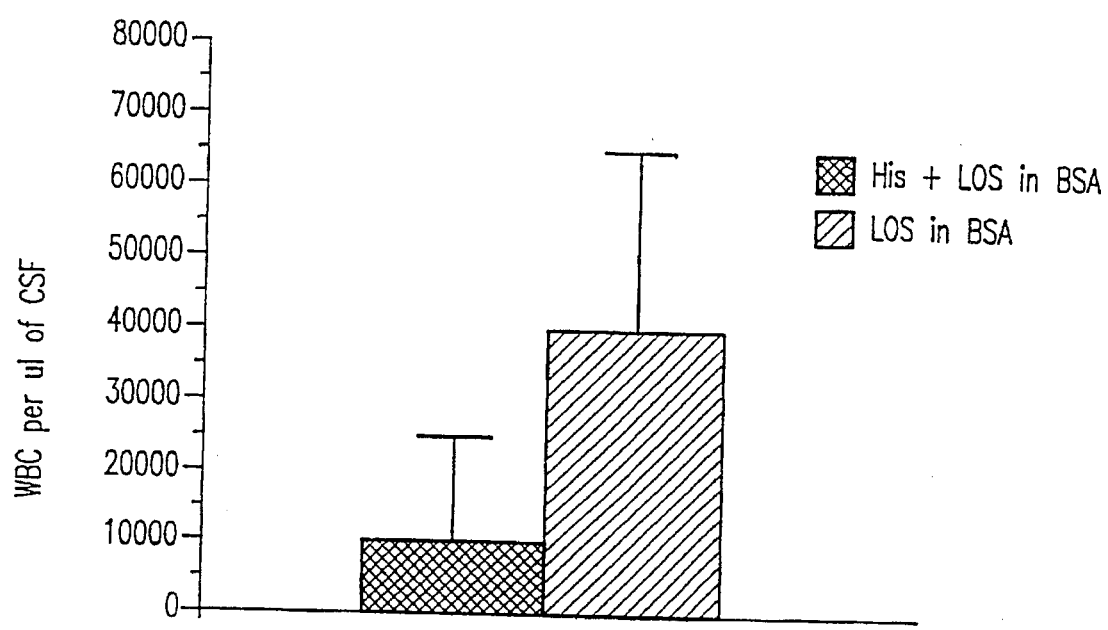
FIG. 4 is a bar graph showing mean white blood cell count±standard deviation of cerebrospinal fluid (CSF) for histidine treated and untreated rats.

FIG. 4 presents the mean white blood cell (WBC) count per µl of CSF for six histidine treated rats (250 mg/kg ip) and six untreated rats administered 20 ng LOS in BSA intracisternally four hours post infection. FIG. 4 shows that histidine treated rats had lower white blood cell counts (p=0.074).

EXAMPLE 3

This Example details experimental results which demonstrate the therapeutic effect of histidine on endotoxin-lung injury (sepsis, septic shock, bacteremia, etc.).

Blood stream infections with bacteria frequently result in injury to the pulmonary vasculature (see, Maunder et al., "Clinical risks associated with the adult respiratory distress syndrome", *Adult Respiratory Distress Syndrome*, Edited by: W. M. Zapol and F. Lemaire, Marcel Dekker: New York, 1991, p. 1–21). Endotoxin administration to animals results in similar lung microvascular injury. Pulmonary vasculature injury can be prevented by agents that deplete neutrophils prior to, during or subsequent to endotoxin injury (Chang, et al., *Journal of Clinical Investigation* 79: 1498–1509, 1987). Ischemia/reperfusion injury is another process in which neutrophils are involved. Horgan, et al., *American Journal of Physiology* 259: L315–L319, 1990, has reported that monoclonal antibodies to the integrin CD18 molecule abolished ischemia/reperfusion injury in the lung.

In the experiment, the effects of L-histidine on endotoxin-injury was evaluated in the chronic catheterized rat model. It has recently been determined that intraperitoneal administration of *Salmonella enteritidis* lipopolysaccharide in a dose of 20 mg/kg results in an increase in pulmonary microvascular permeability to albumin, measured at two hours following endotoxin administration in an isolated buffer perfused rat lung preparation. The positive effects of L-histidine on pulmonary microvascular permeability following endotoxin are evaluated by intravenous administration of a bolus of L-histidine following endotoxin administration, followed by a continuous intravenous infusion for an additional two hour interval until the lungs are removed for measurement of microvascular permeability.

Materials:

$^{125}$I-human serum albumin is obtained from Mallinckrodt Medical, Inc. (Maryland Heights, Mo.). L-histidine (pyrogen-free) is obtained from Westmoreland Pharmaceuticals, L.P., (Charlottesville, Va.). *Salmonella enteritidis* lipopolysaccharide endotoxin and papaverine are obtained from Sigma Chemical Company (St. Louis, Mo.), Rats are obtained from Charles River Labs (Boston, Mass.). Unless otherwise stated, all chemicals for the Greenberg-Bohr buffer are obtained from Sigma Chemical Company (St. Louis, Mo.).

Measurement of pulmonary vascular permeability in the isolated perfused rat lung:

The isolated perfused rat lung model as established by McMurtry et al (*Circulation Research* 38: 99–104, 1976) has been previously employed to measure pulmonary vascular reactivity to alveolar hypoxia (Brashers, et al., *Journal of Clinical Investigation* 82: 1495–1502, 1988). A modification of this model by Chang et al, supra, allows measurement of pulmonary vascular permeability to albumin. For lung evaluation, the animals are deeply anesthetized with pentobarbital sodium, 30 mg/kg i.p., with supplemental doses as needed. Cannulae are then inserted into the pulmonary artery and left ventricle for perfusion and return of effluent from the lung to a reservoir, and the ventilated ($FO_2$=0.21) heart-lung preparation is suspended in a warmed, humidified chamber. Perfusion is instituted at 0.03 ml/gm body weight/minute using a peristaltic pump with Greenberg-Bohr buffer warmed to 37° C. The perfusate buffer contains the following constituents (mM): NaCl (119), KCl (4.7), $MgSO_4$ (1.17), $NaHCO_3$ (19), $KH_2PO_4$ (1.18), $CaCl_2$ (1.6), dextrose (5.5), sucrose (50), and 3% bovine serum albumin (Sigma, Cohn fraction V). Following perfusion with 50 ml of buffer to clear the vasculature of cells, the effluent is returned to the reservoir for recirculation.

Measurement of vascular permeability is performed according to the method of Chang et al, supra. Microvascular hydrostatic pressure is measured by the double occlusion method of Dawson et al. ("Pulmonary microcirculatory hemodynamics", *Annals of the New York Academy of Sciences* 384: 90–106, 1982). To minimize the chance that differences in permeability are due to differences in microvascular hydrostatic pressure, papaverine was added to the reservoir buffer ($1 \times 10^{-4}$M). Ten minutes later, $^{125}$I-human serum albumin, 1 µCi was added to the reservoir buffer, and allowed to equilibrate for 50 minutes. An equilibration sample of buffer is then obtained from effluent, and the $^{125}$I-human serum albumin within the pulmonary vasculature is washed out by changing buffer in the reservoir to 40 mls of fresh buffer without $^{125}$I-albumin. At the end of the washout, a second sample of effluent buffer is obtained. By measuring $^{125}$I using a gamma counter, the "lung leak index" is calculated according to Equation 1.

$$\text{Lung Leak Index} = \frac{\text{Lung total counts per minute (cpm)}}{\text{(Equilibration cpm} - \text{Washout cpm)}} \quad \text{Eq. 1}$$

In accordance with the above protocol, the following three different groups of rats were studied: 1) rats receiving i.p. vehicle (0.9% NaCl) instead of endotoxin and an i.v. bolus of vehicle (1.0 ml) at 60 minutes following endotoxin administration, which is continued as an infusion at 0.6 ml per hour for 60 minutes; 2) rats given a lethal i.p. dose of *Salmonella enteritidis* LPS endotoxin (20 mg/kg body weight) at time 0, with a bolus injection of i.v. vehicle 60 minutes later followed by vehicle infusion for an additional 60 minutes; and 3) rats administered a lethal i.p. dose of endotoxin (20 mg/kg body weight) at time 0, with a bolus injection of L-histidine (100 mg/kg of body weight) in 1.0 ml of 0.9% NaCl vehicle 60 minutes later, followed by an infusion of 50 mg/kg body weight L-histidine for the following 60 minutes. Rats in all three groups were then deeply anesthetized with i.p. pentobarbital, and the heart and lungs were removed for measurement of pulmonary vascular permeability. For the rats in group 3, L-histidine was added to the buffer perfusate at a concentration of 50 mM.

Figure 5:
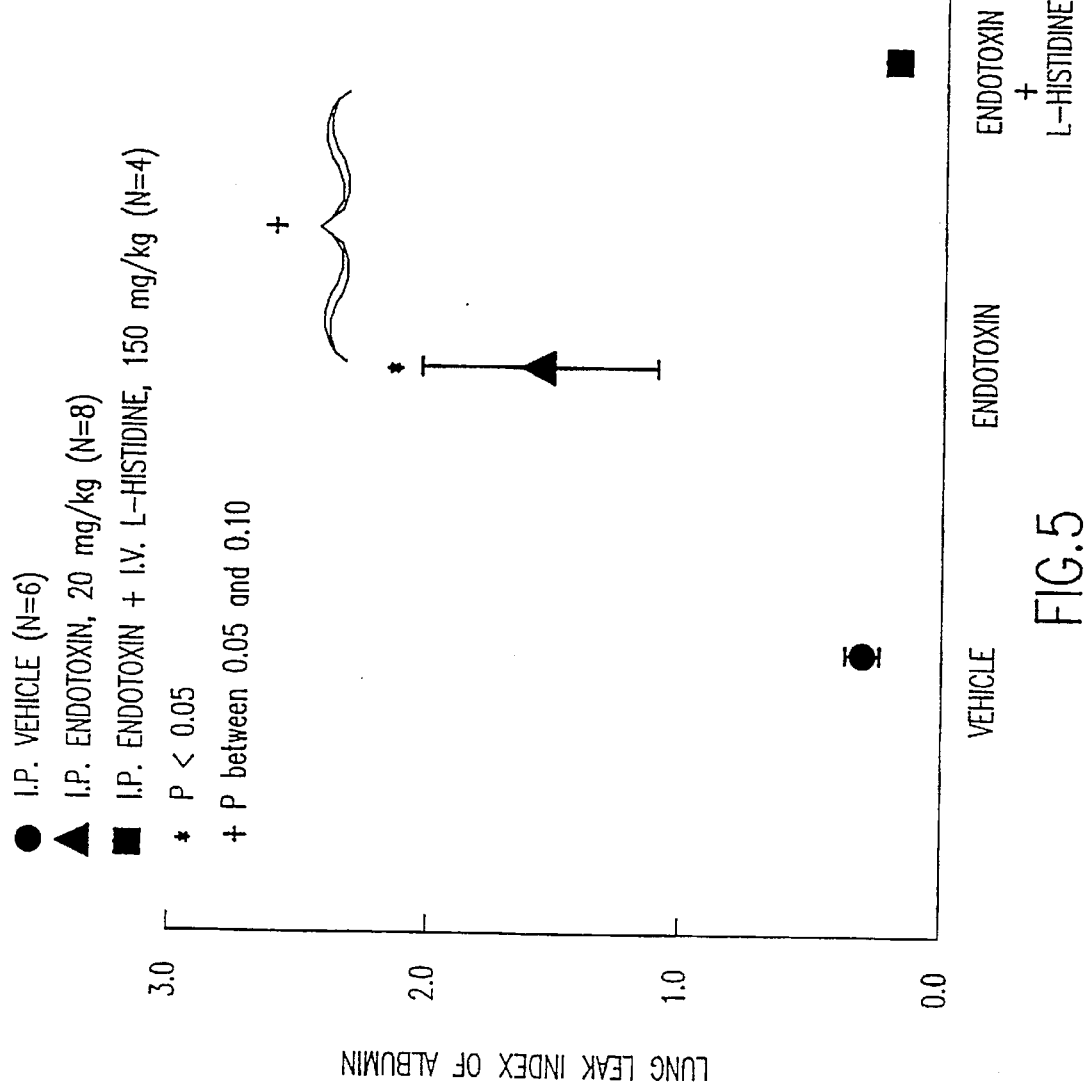
FIG. 5 is a graph showing lung leakage index of albumin for rats treated with endotoxin with and without histidine.

FIG. 5 shows that the four rats in group 3 which received both the endotoxin and the intravenous L-histidine had a Lung Leak Index of Albumin comparable to the six rats in group 1 which received the vehicle only. In sharp contrast, the eight rats in group 2 which only received the lethal dose of i.p. endotoxin had a much higher Lung Leak Index of Albumin. These results demonstrate that the intravenous administration of L-histidine prevents damage to the lung caused by the LPS endotoxin (e.g., the lungs are prevented from becoming highly permeable due to exposure to endotoxin).

EXAMPLE 4

This Example demonstrates the therapeutic effect of histidine on acute phase HTLV-I associated leukemia.

In the experiment, the rabbit model for adult T-cell leukemia (ATL) developed by Sawasdikol et al., "Infection of the Laboratory Rabbit with HIV-1 and HTLV-I", *AIDS Research Reviews*, 2: 211–233, 1992, was used. The work of Sawasdikol et al. has shown that certain rabbit cell lines transformed in vitro with Human T Lymphotrophic Retrovirus Type I (HTLV-I) kills mature outbred New Zealand white rabbits in a dose dependent manner. Several clinical stages of adult T-cell leukemia/lymphoma (ATLL) documented in humans infected with HTLV-I have been observed in rabbits with an HTLV-I transformed rabbit cell line (RH/K34) (see Kindt et al., "Acute Mononuclear Cell Leukemia in Outbred Rabbits inoculated with HTLV-I Transformed Rabbit Lines", *Int'l Cong. Immun.*, August, 1992), and rabbits inoculated with high doses of live cells ($2 \times 10^8$) developed a rapidly fatal leukemia/lymphoma and died due to microvascular thromboembolism and lymphoid necrosis (see, Simpson et al., "Acute Fulminant Stage Adult T-Cell Leukemia/Lymphoma in Rabbits inoculated with HTLV-1 Transformed Rabbit Cell Line", Meeting-Lab of Tumor Cell Biology). Sawasdikol et al., "Acute Mononuclear Cell Leukemia in Outbred Rabbits Inoculated with HTLV-I Transformed Rabbit Cell Lines", *FASEB J.*, Part II, Vol. 6, No. 5, Apr. 5–9, 1992, discloses some cell lines which are capable of killing rabbits in a dose dependent manner within six days after a single intravenous injection.

The objective of this experiment was to determine if it was possible to prevent or delay RH/K34 induced death in rabbits by prophylactic administration of histidine. Eight rabbits were provided with a $3 \times 10^8$ cells injection of an HTLV-I transformed rabbit cell line capable of killing the animals within one week. Four rabbits received a 100 mg/kg body weight dose of L-histidine, and the remaining four rabbits received a 500 mg/kg body weight dose of L-histidine. Amazingly, all eight animals survived for longer than one week, thereby demonstrating that histidine administration can prevent or delay death resulting from leukemia.

The data presented in Examples 1–4 clearly indicate that histidine is an effective agent for combating infectious diseases or pulmonary conditions. As discussed above, the skilled artisan should understand that histidine can be used in various forms, e.g., as a salt, an analog or as a derivative thereof and it could be administered through any suitable route, e.g. intratracheally or intranasally using a nebulizer and the like, orally, intravenously, intrathecally, intramuscularly, suppositorily, transdermally, etc.

While the invention has been described in terms of its preferred embodiments, those skilled in the art will recognize that the invention can be practiced with modification within the spirit and scope of the appended claims.

I claim:

1. A method of providing protection from or amelioration of damage that results from inflammatory responses by tissues arising from at least one of a) infections caused by microorganisms and b) damage from toxins produced by said microorganisms comprising the therapeutic administration, to a patient in need thereof, of L-histidine, or a salt of histidine which can be reduced to L-histidine, in quantities adequate to provide said protection or said amelioration.

2. A method for combating infectious diseases and/or pulmonary conditions, or sequelae thereof comprising the step of administering an effective amount of L-histidine to a patient in need thereof to combat said infectious disease and/or pulmonary condition or sequelae thereof; wherein said step of administering comprises administering L-histidine or a salt of histidine which can be reduced to L-histidine.

3. The method of claim 2 further comprising the step of determining said infectious disease and/or pulmonary condition, or sequelae thereof is produced by *Haemophilus influenzae*.

4. The method of claim 2 further comprising the step of determining said infectious disease and/or pulmonary condition, or sequelae thereof is meningeal inflammation.

5. The method of claim 2 further comprising the step of determining said infectious disease and/or pulmonary condition, or sequelae thereof is produced by *salmonella enteriris*.

6. The method of claim 2 further comprising the step of determining said infectious disease and/or pulmonary condition, or sequelae thereof is selected from the group consisting of sepsis, septic shock, and bacteremia.

7. The method of claim 2 further comprising the step of determining said infectious disease and/or pulmonary condition, or sequelae thereof is produced by human T lymphotrophic retrovirus.

8. The method of claim 2; wherein said step of administering L-histidine is achieved via a route selected from the group consisting of topical, oral, intranasal, intratracheal, transdermal, suppository, intramuscular injection, intrathecal injection, intraperitoneal injection and intravenous injection.

* * * * *